US00RE35568E

United States Patent [19]

Halpern et al.

[11] E Patent Number: Re. 35,568

[45] Reissued Date of Patent: Jul. 22, 1997

[54] METHOD FOR FLUORODECARBOXYLATION

[75] Inventors: Donald F. Halpern, Fanwood, N.J.; Mark L. Robin, W. Laffayette, Ind.

[73] Assignee: Ohmeda Pharmaceutical Products Division Inc., Liberty Corner, N.J.

[21] Appl. No.: 340,960

[22] Filed: Nov. 16, 1994

Related U.S. Patent Documents

Reissue of:

[64] Patent No.: 4,996,371
Issued: Feb. 26, 1991
Appl. No.: 464,834
Filed: Jan. 16, 1990

[51] Int. Cl.[6] ..... C07C 41/00; C07C 19/08; C07C 17/361; C07C 17/00

[52] U.S. Cl. ..... 568/683; 568/684; 568/685; 568/655; 570/142; 570/218; 570/261

[58] Field of Search ..... 568/683, 684, 568/685, 655; 570/142, 218, 261

[56] References Cited

U.S. PATENT DOCUMENTS 3,683,092 8/1972 Regan et al. .
4,469,898 9/1984 Coon et al. .
4,847,427 7/1989 Nappa .
4,874,901 10/1989 Halpern et al. .
4,874,902 10/1989 Huang et al. ..... 568/683

OTHER PUBLICATIONS

Chem tech, May 1989, pp. 304, 308, Halpern.
J. Org. Chem, vol. 48, (1983) pp. 4158–4159, Patrick et al.
Can. J. of Chem., vol. 64, (1986) pp. 138–141, Patrick et al., "Replacement of the Carboxylic Acid Function with fluoride".

*Primary Examiner*—Cynthia Harris Kelly
*Attorney, Agent, or Firm*—R. Hain Swope; Salvatore P. Pace

[57] ABSTRACT

The present invention is directed to a method for replacing a carboxylic acid group with a fluorine [group] in a halogenated aliphatic carboxylic acid compound having the formula, R-COOH, to prepare a fluorinated product having the formula, R-F, wherein R is a halogenated aliphatic group including straight- and branched-chain aliphatic groups selected from the group consisting of halogenated aliphatic and *halogenated* alkoxy-substituted [halogenated] aliphatic groups, wherein the method comprises the step of (a) reacting the halogenated aliphatic carboxylic acid compound with bromine trifluoride, and (b) recovering the fluorinated product.

20 Claims, No Drawings

METHOD FOR FLUORODECARBOXYLATION

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention is directed to a method for preparing fluorinated organic compounds. More particularly, the present invention is directed to a method for the fluorodecarboxylation of halogenated aliphatic carboxylic acid compounds to form fluorinated organic products which are useful as inhalation anesthetics.

2. Description of the Prior Art

Anesthetics belong to a class of biochemical depressant drugs which affect the vital functions of all types of cells, especially nervous tissue cells. General anesthetics produce anlgesia, loss of consciousness, diminished reflex activity, and muscular relaxation, with minimal depression of the vital functions. Anesthetics may be gaseous (volatile) or fixed (nonvolatile). Gaseous anesthetics are inhaled and enter the bloodstream through the lungs and fixed anesthetics are administered parenterally or through the alimentary canal.

Many currently used gaseous anesthetics are halogenated compounds. These compounds tend to cause less metabolic disturbance and are less flammable than traditional gaseous anesthetic compounds such as ether and cyclopropane. Examples of halogenated anesthetic compounds include halothane ($CF_3CHBrCl$) and trichloroethylene ($Cl_2C{=}CHCl$) as well as halogenated ether compounds such as enflurane ($CHF_2OCF_2CHClF$), fluroxene ($CF_3CH_2OCH{=}CH_2$), methoxyflurane ($Cl_2CHCF_2OCH_3$), and isoflurane ($CF_3CHClOCHF_2$).

A particularly useful halogenated ether anesthetic is sevoflurane, $(CF_3)_2CHOCHF_2F$, also known as 2-(fluoromethoxy)-1,1,1,3,3,3,-hexafluoropropane or fluoro-methyl-1,1,1,3,3,3-hexafluoro-2-propyl ether. Sevoflurane has a very low blood-gas solubility partition coefficient (0.6) which provides rapid equilibrium time, fast induction time and rapid recovery time. These properties make it especially useful for outpatient surgery, see D. F. Halpern, Chemtech, pp. 304–308 (May 1989).

The preparation of fluorinated compounds such as sevoflurane tends to be difficult because of the limited number of selective fluorination reactions available. Direct fluorination of organic compounds to replace hydrogen is statistical, non-selective and generally accompanied by the formation of many side products. Hence fluorinated compounds are usually prepared by first synthesizing a substituted organic intermediate, wherein the substituent group is at the site to be fluorinated, and then displacing the substituent group with a fluoride ion. Metal fluorides, for example, have been used to displace chlorine substituent groups.

U.S. Pat. No. 3,683,092, issued to Regan et al., discloses a method for synthesizing sevoflurane which comprises methylation of hexafluorisopropyl alcohol followed by fluorination with either (a) bromine trifluoride or (b) chlorine gas followed by potassium fluoride.

U.S. Pat. No. 4,469,898, issued to Coon et al., discloses a method for synthesizing sevoflurane which comprises mixing hexafluoroisopropyl alcohol, formaldehyde, hydrogen fluoride, and a protonating, dehydrating and fluoride ion generating agent.

U.S. Pat. No. 4,874,901, issued to Halpern et al., discloses a method for fluorinating halogenated ether compounds. In particular, compounds such as sevoflurane can be prepared by reacting chloromethyl hexafluoroisopropyl ether with either potassium fluoride or sodium fluoride.

Patrick et al., J. Org. Chem., 48, 4158–4159 (1983), reports that alkyl carboxylic acids can be fluorodecarboxylated with xenon difluoride ($XeF_2$) in the presence of hydrogen fluoride. Although the use of xenon difluoride on a small scale can be effective, the cost of xenon difluoride makes its use on large scale impractical. Furthermore, when alkoxyacetic acids are fluorodecarboxylated with xenon difluoride, significant amounts of side products are formed.

U.S. Pat. No. 4,847,427, issued to Nappa, discloses a method for preparing fluorocarbon polyethers which comprises neutralizing a perfluorinated carboxylic acid by heating with fluorine in the presence of metal fluoride to replace the carboxylic acid group.

While the above methods are useful for preparing certain fluorinated compounds, these methods are complex, expensive, and often provide fluorinated products in low yield together with considerable amounts of side products. Hence there is a need for improved procedures for the preparation of fluorinated compounds. The present invention provides such an improved procedure for preparing fluorinated compounds from the corresponding carboxylic acids in high yield and purity. More specifically, the present invention provides an improved procedure for the preparation of sevoflurane and other similar types of fluorinated anesthetics.

SUMMARY OF THE INVENTION

The present invention is directed to a method for replacing a carboxylic acid group with a fluorine [group] in a halogenated aliphatc carboxylic acid compound having the formula R—COOH, to prepare a fluorinated product having the formula, R—F, wherein R is a halogenated aliphatic group including straight- and branched-chain aliphatic groups selected from the group consiting of halogenated aliphatic and *halogenated* alkoxysubstituted [halogenated] aliphatic groups, wherein the method comprises the steps of (a) reacting the halogenated aliphatic carboxylic acid compound with bromine trifluoride, and (b) recovering the fluorinated product.

DETAILED DESCRIPTION OF THE INVENTION

The present invention is directed to a method for the fluorodecarboxylation of halogenated aliphatic carboxylic acid compounds to produce fluorinated organic products which are useful as inhalation anesthetics. More particularly, the present invention is directed to a method for replacing a carboxylic acid group with a fluorine [group] in a halogenated aliphatic carboxylic acid compound having the formula, R—COOH, to prepare a fluorinated product having the formula, R—F, wherein R is a halogenated aliphatic group including straight- and branched-chain aliphatic groups selected from the group consisting of halogenated aliphatic and *halogenated* alkoxysubstituted [halogenated] aliphatic groups, wherein the method comprises the steps of (a) reacting the halogenated aliphatic carboxylic acid compound with bromine trifluoride, and (b) recovering the fluorinated product.

More particularly, the present invention is directed at a fluorodecarboxylation method illustrated by equation (1) set out below:

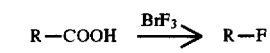

$$R-COOH \xrightarrow{BrF_3} R-F \quad (I)$$

wherin R is a halogenated aliphatic group including straight- and branched-chain aliphatic groups selected from the group consisting of halogenated aliphatic and *halogenated* alkoxy-substituted [halogenated] aliphatic groups. In a preferred embodiment, R is a halogenated lower-alkyl group selected from the group consisting of hexyl, pentyl, butyl, propyl, ethyl, and methyl. In a more preferred embodiment, R is selected from the group consisting of propyl, ethyl, and methyl.

In another preferred embodiment, R is a halogenated lower-alkoxy lower-alkyl group. In a more preferred embodiment, R is a halogenated lower-alkoxy lower-alkyl group wherein the alkoxy group is selected from the group consisting of hexoxy, pentoxy, butoxy, propoxy, ethoxy, and methoxy. In a most preferred embodiment, R is a halogenated lower-alkoxy lower-alkyl group wherein the alkoxy group is selected from the group consisting of hexoxy, pentoxy, butoxy, propoxy, ethoxy, and methoxy, and the alkyl group is selected from the group consisting of hexyl, pentyl, butyl, propyl, ethyl, and methyl.

The term "halogenated aliphatic carboxylic acid compound", as used herein, means an aliphatic carboxylic acid compound sufficiently halogenated such that the compound will not decompose upon contact with bromine trifluoride. Compounds which are insufficiently halogenated will ignite, burn, or otherwise decompose when contacted with bromine trifluoride and will not provide a fluorinated product. The terms "halogenated lower-alkyl group" and "halogenated lower-alkoxy loweralkyl group" similarly mean a lower-alkyl group and a lower-alkoxy lower-alkyl group, respectively, sufficiently halogenated such that the respective groups will not decompose upon contact with bromine trifluoride. The exact degree of halogenation (the number of halogen atoms present in the molecule) and the exact type of halogenation (the type of halogen atoms present in the molecule) may be varied in the aliphatic carboxylic acid compound in order to obtain the desired final fluorinated product. Such variations are within the capabilities of those skilled in the art without the need for undue experimentation.

In another preferred embodiment, the halogenated aliphatic carboxylic acid compound is a fluorinated aliphatic carboxylic acid compound wherein R is a fluorinated aliphatic group including straight- and branched-chain aliphatic groups selected from the group consisting of fluorinated aliphatic and *fluorinated* alkoxy-substituted [fluorinated] aliphatic groups. In a more preferred embodiment, R is a fluorinated lower-alkyl group selected from the group consisting of hexyl, pentyl, butyl, propyl, ethyl, and methyl. In a most preferred embodiment, R is selected from the group consisting of propyl, ethyl, and methyl.

In another preferred embodiment, R is a fluorinated lower-alkoxy lower-alkyl group. In a more preferred embodiment, R is a fluorinated lower-alkoxy lower-alkyl group wherein the alkoxy group is selected from the group consisting of hexoxy, pentoxy, butoxy, propoxy, ethoxy, and methoxy. In a most preferred embodiment, R is a fluorinated lower-alkoxy lower-alkyl group wherein the alkoxy group is selected from the group consisting of hexoxy, pentoxy, butoxy, propoxy, ethoxy, and methoxy, and the alkyl group is selected from the group consisting of hexyl, pentyl, butyl, propyl, ethyl, and methyl.

In a most preferred embodiment, the fluorinated aliphatc carboxylic acid compound is a member selected from the group consisting of [1,1,1,3,3,3-hexafluoro-(2-propoxy) acetic] *2-(1-trifluoromethyl-2,2,2-trifluoroethoxy)acetic* acid and (2,2,2-trifluoroethoxy)acetic acid. In a most preferred embodiment, the fluorinated product is a member selected from the group consisting of 2-fluoromethoxy-1,1,1,3,3,3-hexafluoropropane and fluoromethoxy-2,2,2-trifluoroethane.

[The halogenated aliphatic carboxylic acid starting material compound may be substituted with functional groups providing such groups do not react with bromine trifluoride under the reaction conditions. In general, non-reactive functional groups which may be present in the starting material include alkoxy groups, aryloxy groups, and mixtures thereof.]

The term "lower-alkyl", as used herein, means branched- or unbranched-hydrocarbon groups containing from 1 to 6 carbon atoms, and preferably from 1 to 4 carbon atoms. The term "lower-alkoxy", as used herein, means branched or unbranched hydrocarboxy groups containing from 1 to 6 carbon atoms, and preferably from 1 to 4 carbon atoms. The term "halogen", as used herein, refers to the chemically related elements consisting of fluorine, chlorine, bromine and iodine, and preferably fluorine.

Bromine trifluoride ($BrF_3$) is a colorless liquid having a melting point of 8.77° C. In general, bromine trifluoride will be present in the reaction mixture in a stoichiometric excess compared to the total amount of halogenated aliphatic carboxylic acid compound. A 1:1 molar ratio of bromine trifluoride to halogenated aliphatic carboxylic acid compound, respectively, represents a 3:1 equivalent ratio with respect to fluorine. In a preferred embodiment, bromine trifluoride and the halogenated aliphatic carboxylic acid compound will be present in the reaction mixture in an equivalent ratio from about 2:3 to about 3:1, more preferably in an equivalent ratio from about 2:3 to about 1:1, and most preferably in an equivalent ratio of about 2:3, respectively.

When the halogenated aliphatic carboxylic acid starting material compound is liquid, the fluorodecarboxylation reaction may be carried out without solvent. When the halogenated aliphatic carboxylic acid compound is not liquid, the fluorodecarboxylation reaction may be carried out in an inert solvent. Useful inert solvents include, but are not limited to, highly halogenated compounds such as dichloromethane (methylene chloride), chloroform, carbon tetrachloride, trifluoromethane, perfluorodecalin, and the like, and mixtures thereof. In a preferred embodiment, the inert solvent is carbon tetrachloride.

The temperature of the fluorodecarboxylation reaction is not critical, but reaction usually taken place at room temperature. The temperature of the reaction mixture may be maintained at just above the boiling point of the fluorinated product to permit distillation of the product concurrent with its synthesis, thereby reducing degradation of the product when exposed to the harsh conditions of the fluorodecarboxylation reaction mixture.

The fluorinated product may be also be recovered from the reaction mixture in an other known fashion. For example, the reaction mixture may be warmed to a temperature sufficient to decompose excess bromine trifluoride by reaction with the solvent (a temperature of about 50° C. is generally sufficient in the presence of carbon tetrachloride). The reaction mixture may then be washed with sodium bisulfide ($NaHSO_3$) and the organic layer separated.

The compounds which may be prepared by the fluorodecarboxylation method of the present invention include compounds which posses very desirable anesthesia activities. In particular, the anesthetic compounds which may be prepared have central nervous system depressant properties which include analgesia, hypnosis, sedation, increased pain threshold, and barbiturate and/or general anesthetic potentiation. Many of the compounds provide highly potent anesthesia with immediate onset and a short duration of action. These properties are highly desirable in circumstances where acute severe pain must be eliminated over a short period of time, such as in anesthesiology. The preferred compounds provide reduced rigidity at high doses, superior motor coordination recovery, or less respiratory depressive and/or cardiovascular depressive activity.

The present invention is further illustrated by the following examples which are presented for the purpose of demonstrating, but not limiting, the method of this invention.

EXAMPLE 1

[1,1,1,3,3,3-Hexafluoro-(2-propoxy)acetic] *2-(1-trifluoromethyl-2,2,2-trifluoroethoxy)-acetic* acid.

This Example illustrates a method for preparing a halogenated aliphatic carboxylic acid starting material compound according to the present invention.

A solution of [1,1,1,3,3,3-hexafluoro-2-propanol] *1-trifluoromethyl-2,2,2-trifluoroethanol* (42.1 g, 0.25 mole, Aldrich) and bromoacetic acid (69.5 g, 0.5 mole) in water (150 ml) was brought to pH 12.5 by addition of 50% sodium hydroxide solution (47 g) with stirring and maintained at pH 12.5±0.5 by addition of 50% sodium hydroxide solution, as needed. The reaction solution was heated to reflux for 3.5 hours, then cooled. A solution of 37% hydrochloric acid (61.3 g) and 8% hydrochloric acid (27.1 g) was added to the reaction solution to bring the pH to 1. The reaction solution was then distilled (azeotrope) under a Dean-Stark trap. The lower layer in the Dean-Stark trap was separated (53.2 g) and sublimed (88° C., 7–9 mm, dry ice/acetone trap) to yield 27.12 g (48% yield) of [1,1,1,3,3,3-hexafluoro-(2-propoxy) acetic] *2-(1-trifluoromethyl-2,2,2-trifluoroethoxy)acetic* acid having mp. 60°–62° C.

When chloracetic acid was substituted from bromoacetic acid in the above procedure, a 19.8% yield of [1,1,1,3,3,3-hexafluoro-(2-propoxy)acetic] *2-(1-trifluoromethyl-2,2,2-trifluoroethoxy)acetic* acid was obtained.

EXAMPLE 2

2-Fluoromethoxy-1,1,1,3,3,3-hexafluoropropane.

This Example illustrates the fluorodecarboxylation of a halogented aliphatic carboxylic acid compound to a fluorinated product according to the method of the present invention.

A solution of [1,1,1,3,3,3-hexafluoro-(2-propoxy)acetic] *2-(1-trifluoromethyl-2,2,2-trifluoroethoxy)acetic* acid (2.26 g, 0.01 mole) from Example 1 in carbon tetrachloride (100 g) was introduced into a 400 ml Teflon vessel equipped with an air-tight cover, a thermometer, a Teflon stirring bar, a bromine trifluoride inlet and a gas outlet connected to a dry ice/acetone trap. Bromine trifluoride (1.05 g, 0.42 ml, 0.0067 mole) was slowly added to the solution. When addition of bromine trifluoride was complete, the reaction mixture was heated gently to just under reflux for 5 hours to remove volatiles and decompose excess bromine trifluoride (by reaction with carbon tetrachloride). The reaction mixture was then cooled and washed with dilute sodium bisulfite ($NaHSO_3$) solution. The organic layer was separated and analysis by gas chromatography showed a 75% yield of the product 2-fluoromethoxy-1,1,1,3,3,3-hexafluoropropane.

EXAMPLE 3

(2,2,2-Trifluoroethoxy)acetic acid.

This Example illustrates another method for preparing a halogenated aliphatic carboxylic acid starting material compound according to the present invention.

A solution of 2,2,2,-trifluoroethanol (84 g, 1 mole, Aldrich) and chloroacetic and (189 g, 2 moles) in water (600 ml) was brought to pH>13 by addition of 50% sodium hydroxide solution with stirring and maintained at pH>13 by addition of 50% sodium hydroxide solution, as needed. The reaction solution was heated to 84°–93° C. for 3.5 hours, maintained at 90°–100° C. overnight, then cooled. Concentrated hydrochloric acid was added to the reaction solution to bring the pH to about 1. The reaction solution was then heated until all 2,2,2-trifluoroethanol was distilled. The reaction solution was then cooled and extracted 12 times with dichloromethane (250 ml portions). The combined dichloromethane extracts were concentrated under vacuum to yield 104.3 g of residue which was taken up in acetone (200 ml). The acetone mixture was filtered to remove inorganic salts, concentrated under vacuum, then distilled in two fractions (the first fraction distilled at 93°–94.9° C. at 4.6 mm/Hg and the second fraction distilled at 95.1°–95.2° C. at 4.6 mm/Hg). The two fractions were combined to afford 87.9 g of the product (2,2,2-trifluoroethoxy)acetic acid.

Anal. Calculated for $C_4H_5F_3O_2$: C, 30.38% H, 3.16%. Found C, 30.35%; H, 3.00%.

EXAMPLE 4

Fluoromethoxy-2,2,2-trifluoroethane.

This Example illustrates the fluorodecarboxylation of another halogenated aliphatic carboxylic acid compound to a fluorinated product according to the method of the present invention.

A solution of (2,2,2-trifluoroethoxy)acetic acid (2.2 g, 0.0014 mole) from Example 3 in carbon tetrachloride (80 g) was introduced into a 400 ml Teflon vessel equipped with an air-tight cover, a thermometer, a Teflon stirring bar, a bromine trifluoride inlet and a gas outlet connected to a dry ice/acetone trap. Bromine trifluoride (5.7 g, 2 ml, 0.041 mole) was slowly added to the solution. When addition of bromine trifluoride was complete, the reaction mixture was heated gently to just under reflux for 5 hours to remove volatiles and decompose excess bromine trifluoride (by reaction with carbon tetrachloride). The reaction mixture was then cooled and washed with dilute sodium bisulfite solution. The organic layer was separated and analysis by gas chromatography showed a 90% yield of the product fluoromethoxy-2,2,2-trifluoroethane.

EXAMPLE 5

Fluoromethoxy-2,2,2-trifluoroethane.

This Example illustrates the fluorodecarboxylation of another halogenated aliphatic carboxylic acid compound to a fluorinated product according to the method of the present invention.

A solution of (2,2,2-trifluoroethoxy)acetic acid (20.0 g, 0.127 mole) from Example 3 in dichloromethane (229.3 g)

was introduced into a 400 ml Teflon vessel equipped with an air-tight cover, a thermometer, a Teflon stirring bar, a bromine trifluoride inlet and a gas outlet connected to a dry ice/acetone trap. The vessel was placed in a water bath at room temperature and bromine trifluoride (11.4 g, 4 ml, 0.084 mole) was slowly added to the solution. When addition of bromine trifluoride was complete, the reaction mixture was stirred overnight, then washed with dilute sodium bisulfite solution. The organic layer was separated (194 g) and analysis by gas chromatography showed a 100% yield of the product fluoromethoxy-2,2,2-trifluoroethane.

EXAMPLE 6

Fluoromethoxy-2,2,2-trifluoroethane.

This Example illustrates the fluorodecarboxylation of a halogenated aliphatic carboxylic acid compound to a fluorinated product using xenon difluoride.

Xenon difluoride (2 g, 0.012 mole) was slowly added over a period of one hour to a solution of (2,2,2-trifluoroethoxy) acetic acid (1.9 g, 0.012 mole) from Example 3 in carbon tetrachloride (20 g) in a glass vessel. When addition of xenon difluoride was complete, the reaction mixture was heated to 45° C. for 0.5 hour, then cooled. The reaction mixture was then diluted to provide 0.44 of product (25% yield). Gas chromatography analysis showed the major product to be fluoromethoxy-2,2,2-trifluoroethane contaminated with significant amounts of $CF_3CH_2OCF_2H$, $CF_3CHFOCH_2F$, $CF_2Cl_2$, and $CFCl_3$.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:

1. A method for replacing a carboxylic acid group with a fluorine [group] in a halogenated aliphatic carboxylic acid compound having the formula, R-COOH, to prepare a fluorinated product having the formula, R-F, wherein R is a halogenated aliphatic group including straight- and branched-chain aliphatic groups selected from the group consisting of halogenated aliphatic and *halogenated* alkoxy-substituted [halogenated] aliphatic groups, wherein the method comprises the steps of:

(a) reacting the halogenated aliphatic carboxylic acid compound with bromine trifluoride; and (b) recovering the fluorinated product.

2. The method according to claim 1, wherein R is a halogenated aliphatic group selected from the group consisting of hexyl, pentyl, butyl, propyl, ethyl, and methyl.

3. The method according to claim 1, wherein R is a halogenated lower-alkoxy lower-alkyl group.

4. The method according to claim 3, wherein the lower-alkoxy group is selected from the group consisting of hexoxy, pentoxy, butoxy, propoxy, ethoxy, and methoxy.

5. The method according to claim 1, wherein bromine trifluoride and the halogenated aliphatic carboxylic acid compound are present in an equivalent ratio from about 2:3 to about 3:1 respectively.

6. The method according to claim 5, wherein bromine trifluoride and the halogenated aliphatic carboxylic acid compound are present in an equivalent ratio from about 2:3 to about 1:1, respectively.

7. The method according to claim 1, wherein the halogenated aliphatic carboxylic acid compound is reacted with bromine trifluoride in an inert solvent.

8. The method according to claim 7, wherein the inert solvent is selected from the group consisting of dichloromethane, chloroform, carbon tetrachloride, and mixtures thereof.

9. The method according to claim 1, wherein the halogenated aliphatic carboxylic acid compound is a fluorinated aliphatic carboxylic acid compound.

10. The method according to claim 9, wherein R is a fluorinated aliphatic group selected from the group consisting of hexyl, pentyl, butyl, propyl, ethyl, and methyl.

11. The method according to claim 9, wherein R is a fluorinated lower-alkoxy lower-alkyl group.

12. The method according to claim 11, wherein the lower-alkoxy group is selected from the group consisting of hexoxy, pentoxy, butoxy, propoxy, ethoxy, and methoxy.

13. The method according to claim 9, wherein bromine trifluoride and the fluorinated aliphatic carboxylic acid compound are present in an equivalent ratio from about 2:3 to about 3:1, respectively.

14. The method according to claim 13, wherein bromine trifluoride and the fluorinated aliphatic carboxylic acid compound are present in an equivalent ratio from about 2:3 to about 1:1, respectively.

15. The method according to claim 9, wherein the fluorinated aliphatic carboxylic acid compound is reacted with bromine trifluoride in an inert solvent.

16. The method according to claim 15, wherein the inert solvent is selected from the group consisting of dichloromethane, chloroform, carbon tetrachloride, and mixtures thereof.

17. The method according to claim 9, wherein the fluorinated aliphatic carboxylic acid compound is [1,1,1,3,3,3-hexafluoro-(2-propoxy)acetic] *2-(1-trifluoromethyl-2,2,2-trifluoroethoxy)acetic* acid.

18. The method according to claim 9, wherein the fluorinated aliphatic carboxylic acid compound is (2,2,2-trifluoroethoxy)acetic acid.

19. The method according to claim 9, wherein the fluorinated product is 2-fluoromethoxy-1,1,1,3,3,3-hexafluoropropane.

20. The method according to claim 9, wherein the fluorinated product is fluoromethoxy-2,2,2-trifluoroethane.

* * * * *